(12) United States Patent
Meiss et al.

(10) Patent No.: US 8,286,510 B2
(45) Date of Patent: Oct. 16, 2012

(54) FORCE SENSOR AND METHOD FOR DETECTING AT LEAST ONE FORCE COMPONENT

(76) Inventors: Thorsten Meiss, Fürth (DE); Thorsten Kern, Alsbach (DE); Stephanie Sindlinger, Dieburg (DE); Roland Werthschützky, Kleinmachnow (DE)

( * ) Notice: Subject to any disclaimer, the term of this patent is extended or adjusted under 35 U.S.C. 154(b) by 571 days.

(21) Appl. No.: 12/306,886

(22) PCT Filed: Jun. 29, 2007

(86) PCT No.: PCT/DE2007/001153
§ 371 (c)(1),
(2), (4) Date: Jul. 29, 2009

(87) PCT Pub. No.: WO2008/000246
PCT Pub. Date: Jan. 3, 2008

(65) Prior Publication Data
US 2010/0024574 A1    Feb. 4, 2010

(30) Foreign Application Priority Data
Jun. 29, 2006 (DE) .......................... 10 2006 030 407

(51) Int. Cl.
*G01L 1/04* (2006.01)
*G01L 1/22* (2006.01)
(52) U.S. Cl. ......... 73/862.634; 73/862.629; 73/862.621; 73/862.637
(58) Field of Classification Search ............... 73/862.68, 73/862.621–862.622, 862.625, 862.627–862.629, 73/862.632, 862.634, 862.636, 862.639, 73/862.041–862.046
See application file for complete search history.

(56) References Cited

U.S. PATENT DOCUMENTS

| 3,261,204 A |   | 7/1966  | Jacobson |            |
|-------------|---|---------|----------|------------|
| 4,299,130 A | * | 11/1981 | Koneval  | 73/862.628 |
| 4,325,048 A | * | 4/1982  | Zaghi et al. | 73/862.634 |

(Continued)

FOREIGN PATENT DOCUMENTS
DE    3940696 A1    6/1991
(Continued)

OTHER PUBLICATIONS

Beccai et al., "Silicon-Based Three Axial Force Sensor for Prosthetic Applications", Proccedings of the 7th Italian Conference on Sensors and Microsystems, Feb. 4-6, 2002, pp. 250-255.

*Primary Examiner* — Lisa Caputo
*Assistant Examiner* — Jonathan Dunlap
(74) *Attorney, Agent, or Firm* — The Webb Law Firm (57) ABSTRACT

A force sensor for detecting at least a force acting in a longitudinal direction of a catheter or guide wire, the force sensor comprising a force pick-up for detecting the force, wherein the force pick-up comprises: a base body with an end face, wherein the base body includes at least one cutout, wherein the cutout causes an asymmetry of the base body relative to the longitudinal direction of the catheter or guide wire upon flexing of the base body upon force $F_z$ loading thereon from an axial direction, wherein the end face includes a surface area that is substantially greater than the cross-sectional area of the base body in the region of the cutout, but not substantially smaller than the cross-section of the rest of the base body. A method for using this force sensor is also disclosed.

19 Claims, 4 Drawing Sheets

U.S. PATENT DOCUMENTS

| | | | |
|---|---|---|---|
| 4,331,035 A * | 5/1982 | Eisele et al. | 73/862.632 |
| 4,718,287 A * | 1/1988 | Mishliborsky | 73/862.632 |
| 4,748,858 A | 6/1988 | Ort | |
| 4,787,256 A * | 11/1988 | Cherbuy | 73/862.628 |
| 5,079,535 A * | 1/1992 | Neuman et al. | 73/862.627 |
| 5,129,265 A | 7/1992 | Bartels et al. | |
| 5,132,658 A | 7/1992 | Dauenhauer et al. | |
| 5,207,103 A | 5/1993 | Wise et al. | |
| 5,396,887 A | 3/1995 | Imran | |
| 5,522,266 A | 6/1996 | Nicholson et al. | |
| 5,988,000 A * | 11/1999 | Adams | 73/862.044 |
| 6,221,023 B1 * | 4/2001 | Matsuba et al. | 600/486 |
| 7,097,620 B2 | 8/2006 | Corl et al. | |
| 7,967,762 B2 | 6/2011 | Corl et al. | |
| 2005/0011272 A1 * | 1/2005 | Tenerz | 73/756 |
| 2010/0307265 A1 * | 12/2010 | Werthschutzky et al. | 73/862.68 |

FOREIGN PATENT DOCUMENTS

| | | |
|---|---|---|
| DE | 10303270 A1 | 8/2004 |
| DE | 10319081 A1 | 12/2004 |
| EP | 0176173 | 4/1986 |
| JP | 6190050 A | 7/1994 |
| JP | 2006064465 | 3/2006 |

* cited by examiner

FORCE SENSOR AND METHOD FOR DETECTING AT LEAST ONE FORCE COMPONENT

BACKGROUND OF THE INVENTION

1. Field of the Invention

The invention relates to a force sensor for preferred application on the tip of an elongated device, and to a method for measuring a force and the effective direction thereof.

2. Description of Related Art

A particular case of application of this invention relates to catheter technology, which is defined by an elongated device for at least partial insertion into an organism through a body orifice. These elongated devices are used primarily in minimally invasive surgery and diagnosis on, in particular human, bodies. In order that, during the invasion of the elongated device, no body vessels are injured by a tip, in the vicinity of the body, of the elongated device, which is generally to be operated manually by the treating physician, the physician necessarily orients himself by what forces are conveyed to him at a handle of the elongated device. Owing to the friction and the inserted catheter/guide wire mass that increases continuously in the course of the invasion of the catheter or guide wire into the body, the force conveyed to the treating physician at the handle provides virtually no useful information about the forces actually occurring at the catheter/guide wire tip. In order that the treating physician can convey the correct actuating force to the handle of the catheter, this requires an extremely extensive wealth of experience in operating catheter/guide wires.

DE 103 03 270 A1 discloses a catheter arrangement in which the force acting on the catheter tip during insertion is measured. The corresponding force is conveyed to the physician in tactile fashion via a haptic handle. This makes it easier to find for example blood vessel junctions or perforations at the heart septum, especially for an inexperienced physician, and forms the basis for intuitive handling of the device. An electrodynamic drive device that serves for generating the haptic force prestress and uses a measurement variable representing the force of the tip is known from DE 103 19 081. The invention presented here permits the force measurement at the tip of the elongated device and the evaluation of the measurement signals, which is necessary for implementing the invention from DE 103 03 270 A1.

In accordance with U.S. Pat. No. 6,221,023 B1, a force sensor based on resistive functional operation is provided at the tip of catheters. The force introduced into the sensor is picked up by a resistance bridge circuit. The construction of this sensor involves a high outlay on account of the large number of parts. The associated manufacturing and assembly costs make the known sensor unsuitable particularly for catheters on account of the preferred disposable property thereof. Furthermore, the area for primary contact-connection of the measuring element is embodied perpendicular to the longitudinal direction of the catheter and the area for contact-connection is therefore limited by the diameter of the elongated device. Therefore, and owing to the high number of parts, the miniaturizability of the force sensor in particular below a catheter diameter of less than 3 mm can be realized only with an extremely high structural outlay. On account of the large dimensions it can be inferred that the sensor completely closes the catheter tube at the tip. This means, however, that the function of the catheter tube, through which instruments and fluids are introduced into the body, is no longer expediently provided. It is not possible to integrate the sensor into the significantly thinner guide wire required in catheterizations, on account of the large dimensions, the high number of parts and the unfavorable wire guidance through the contact area oriented perpendicular to the longitudinal direction.

JP 06190050 A describes a tactile sensor that can be fitted to the outer wall of catheters. It is proposed to produce this sensor from a very thin silicon wafer. However, very thin elements cannot pick up the forces of approximately 300 mN that occur. The use of thicker, stabler silicon wafers is ruled out since bending of thicker wafers, which is necessary for integration into the device, would lead to the material breaking apart.

"Beccai L et al.: *Silicon-based three axial Force Sensor for Prosthetic Applications. Sensors and Microsystems, Proceedings of the 7th Italian Conference* 2002" presents a force sensor that is intended to be integrated into leg prostheses. The force vector can be determined by measuring the force in terms of direction and amplitude. Resistive elements are used for measuring the forces, said resistive elements not being connected up to form a "Wheatstone bridge". For integration into an elongated device, however, bridge interconnections should be striven for, whereby a high measuring accuracy can be obtained since the signals can then be transmitted virtually independently of lead resistances of the long, thin leads. Precisely in the case of long devices inserted into the body, the measurement signal is otherwise dependent on the temperature of the lead and thus on the insertion length of the device. The production of the elements requires an expensive multistage dry etching process on both sides. The measuring element nevertheless additionally has to be mounted over a special counter-body in order to enable the measuring beams to be deflected. The sensor therefore comprises at least two parts which have to be connected to one another exactly. Owing to the dictates of the construction, the exposed force pick-up, called a mesa, has a great length, namely approximately a length corresponding to the thickness of the starting material. Consequently, this sensor fundamentally always exhibits a measuring sensitivity that is higher by a multiple, but also susceptibility to destruction, relative to lateral forces, in comparison with the force acting in the longitudinal direction. That is unfavorable since it is desirable to measure particularly the forces in the longitudinal direction of the device or to obtain a balanced sensitivity for different force components. The measuring element has a plane of the electrical contacts that is perpendicular to the longitudinal direction, such that the contact-connection area is limited to the diameter of the installation area, which makes contact-connection more difficult. The measuring element has a large diameter of approximately 1 mm relative to guide wires, such that integration into the guide wire is not possible.

This shows that the prior art of tactile sensors for integration into catheters does not meet the requirements made with regard to miniaturization, high stability, simple production and low costs.

SUMMARY OF THE INVENTION

It is an object of the invention to specify a force sensor of the generic type mentioned above which is constructed in a simple manner and comprises one part, which can be integrated into elongated devices having a diameter of less than 3 mm, in particular 0.33 mm diameter (1 French), and can detect forces which act at least partly on the elongated device in the longitudinal direction. Furthermore, the intention is to make it possible to convey a force-dependent torque to the user, with detection of the force vector present at the guide wire tip, that is to say determination of the force magnitude in three independent directions, preferably also to enable a conclusion to be drawn about the direction of the force acting, and thus to determine forces according to magnitude and direction.

Accordingly, the sensor according to the invention is designed to detect a force acting on the elongated device, in particular an elongated medical device such as a catheter or guide wire, which force can have a non-negligible force component in the longitudinal direction of the elongated device. The sensor according to the invention has a force pick-up, at which at least the substantial part of the force to be detected can be introduced either via the elongated device or in a manner directed directly into the sensor. The sensor is intended to be constituted according to the invention in such a way that it can be fitted to the elongated device, and in particular can be retrofitted in already existing elongated devices. According to the invention, the sensor has at least one end face which has a non-negligible area size in relation to the cross-sectional area of the sensor and enables the coupling in particularly of the forces having a force component in the longitudinal direction of the elongated device in a special way. The simple miniaturization of the force sensors furthermore permits the integration of the force sensors into the catheter wall, without closing off the distal catheter opening and also the particularly important and demanding integration into the guide wire. By means of particular constructional features and the application of a method for obtaining signals, it is possible to determine the forces on the elongated device in terms of amplitude and furthermore also in terms of the effective direction.

The sensor according to the invention affords the following advantages over the known force sensors mentioned:
- the sensor according to the invention affords the possibility of integrating a force sensor system into elongated devices having a lateral extent or a diameter of less than 3 mm, in particular 0.33 mm (1 French);
- the sensor according to the invention comprises a single part and is outstandingly suitable for mass production on account of the small number of parts and the manufacturing technology in the wafer assemblage. The manufacturing costs are very low, mounting costs for the sensor element itself are obviated, and mounting on the elongated device is simple;
- the particular configuration and the associated high mechanical stiffness enable a very simple, thin, cost-effective housing and thus readily satisfy the stringent requirements for hygiene in medical technology;
- with the sensor according to the invention, on account of the preferred use of the piezoresistive effective principle, very accurate force magnitude and force direction measurements can be obtained, using a cost-effective external evaluation electronic unit;
- extremely accurate measurements can be effected with the sensor according to the invention on account of the usability of preferably silicon as a basic material, such that in the event of force loading and relief, the output signal reproduces the force present to a particular extent;
- using currently available technology, the sensor according to the invention can also be miniaturized far below the required lateral dimensions of 0.3 mm;
- additional electronics can be monolithically integrated on the sensor according to the invention in a simple manner, such that the disturbing influences of the signal transmission, but in particular also the number of electrical supply lines required can be reduced to a minimum. The components of the elongated device that are already present can be used for power and signal transmission, whereby the costs of the entire device are increased only very little by the sensor integration.

The sensor according to the invention can detect forces according to the magnitude and/or the effective direction in real time, and in particular continuously. In particular, the sensor according to the invention is designed to detect a force principally in the longitudinal direction of the elongated device.

The sensor according to the invention is constructed from a base element having at least one lateral incision. An asymmetry of the base body arises on account of said incision, such that a flexure of the measuring element is effected in the event of force loading in the longitudinal direction of the elongated device. Said flexure generates mechanical stresses, which are preferably detected in the vicinity of the incision by means of stress- and strain-sensitive resistors. The change in these measuring resistors thus reproduces the force present in a proportional ratio. A force coupled in in an axial direction generates, in the measuring element in regions having the same thickness, a stress state that is constant over the length of the measuring element, while the mechanical stresses which result from lateral coupling in of force are greatly dependent on the location on the measuring element. By integrating at least one resistor for each force component to be measured, it is also possible to determine the complete force vector besides the axial force. A method is described for this.

All the embodiments can be fabricated by microfabrication methods, preferably those of bulk micromachining in silicon. In this case, a silicon wafer is patterned in such a way that resistors are produced by introducing a dopant into the silicon, which resistors change the magnitude of their resistance in a manner dependent on the mechanical stress. These resistors are electrically conductively connected only at the desired regions on account of the electrical effect between the silicon wafer and the effect of the dopant, otherwise they are insulated from one another on account of the chosen production by formation of a pn junction. On account of the simpler production, these resistors are generally introduced on the top side of the measuring element rather than in depressions in the silicon wafer, as will also be assumed hereinafter. An increase in the measuring sensitivity can be achieved in the sensor according to the invention, however, if the resistors are introduced on the rear side of the bending plate in the incision, for example by patterning using thick-film resist. The methods of micropatterning make it possible to produce an extremely large amount of sensors simultaneously on a wafer (batch method, fabrication in panel) and thus enable very cost-effective measuring elements. All the fabrication methods mentioned here are established prior art, e.g. in the fabrication of pressure and force sensors.

Besides the embodiment as a miniaturized piezoresistive measuring element, it is generally also possible to construct the measuring elements presented in a macroscopic manner, for example using metal as base body material, and to use strain gauges for stress and/or strain measurement. Instead of applying resistors introduced by doping, it is also possible to apply stress- or strain-dependent resistors of a different configuration, for example using thick- or thin-film technology.

The different variants with a monocrystalline base body composed of silicon that are set out below constitute preferred variants for various production methods.

The first embodiment is distinguished by the fact that the patterning of the incision of the base body can be produced by the readily available technology of the wet-chemical etching of silicon by means of KOH, for example. This technology is distinguished by low capital expenditure, such that it can also be employed by medium-sized companies. The production can be effected in the manner as employed in the case of standard pressure sensors in which the membrane thickness is determined by the etching time. Production methods with an electrochemical etching stop at an epitaxial layer are also possible for force measuring elements for very small nominal forces.

In a further embodiment, the incision of the base body is produced by dry etching from the rear side of the wafer. The high aspect ratio of the steep etching edge makes it possible to position the cutout very close to the top plate and thus to measure axial forces very sensitively with the measuring element, but to obtain a low sensitivity for lateral forces $F_x$ and $F_y$. In this fabrication variant it is also possible to set the sensitivity of the measuring element for different force directions by means of the position of the cutout. This forms the basis for particularly powerful sensors for three-dimensional force measurement. The positioning of the cutout close to the top plate furthermore increases the stiffness of the base body and thus reduces influences of the housing in the case of a potting with plastic, and furthermore enables particularly dynamic measurements.

In a further embodiment, the incision of the base body is produced by sawing from the rear side of the wafer. Alternative micromachining methods such as grinding, polishing, eroding and drilling methods can also be used instead of sawing. However, sawing is a very expedient method for production since sawing is generally also used for singulating the patterned measuring elements from the wafer. Consequently, the singulation of the measuring elements and the production of the measuring elements can be effected virtually simultaneously by means of the same process, preferably from the rear side of the wafer. Measuring elements can in this way be produced extremely simply and cost-effectively with just two mask steps, namely for doping and for conductor track patterning, and without etching technology. Furthermore, a virtually perpendicular edge of the incision can be produced. Therefore, the incision, as in the application of dry etching, can be introduced close to the top plate of the base body. This increases the functionality of the measuring element since lateral force components have a smaller influence on the measurement result. Furthermore, a plurality of process steps are obviated in the patterning of the incision since a patterning of an etching mask on the rear side of the wafer can be obviated. These steps are specifically a plurality of cleaning steps, the application and patterning of the etching mask, the etching, etc. The method can be carried out by wafer sawing. In order to increase the stability of the measuring element, a brief chemical etching step can subsequently be effected in order to reduce microcracks, but this does not require the rear side to be masked. In this case, it is also possible, furthermore, for the outer edges of the measuring element to be rounded and possible tolerances of the sawing process to be compensated for very exactly and simply. This embodiment therefore affords all the advantages of the previous variant produced by dry etching, with reduction of the process steps and with use of very cost-effective production technologies. The processing order of the steps described can be varied within specific limits according to the apparatuses used.

In a further embodiment, the cutout for producing the asymmetry is produced not only by a straight incision on the rear side of the wafer, but for example by drilling or special etching holes in the rear side of the wafer or in the front side of the wafer. This gives rise to a higher asymmetry of the measuring element. The measuring effect is increased further as a result.

A further embodiment arises by virtue of the processing of measuring elements used as standard in pressure measuring technology. In the case of pressure sensors, a thinning of the base body below the measuring resistors is attained by means of an etching process. These measuring elements always have a stable edge structure. By removing this edge structure, for example by sawing or etching, this structure of a pressure measuring element can be converted into a structure according to the invention.

Finally, the invention relates to a method for determining the magnitude of the force acting on the elongated device. Further embodiments of this method make it possible, in particular, to determine the force according to magnitude and direction.

The sensors can be used for example at the tip of guide wires, but also at any desired location in catheters.

BRIEF DESCRIPTION OF THE DRAWINGS

Further advantages, features and properties of the invention will become clear from the following description of preferred embodiments of the invention with reference to the accompanying drawings, in which.

DETAILED DESCRIPTION OF THE INVENTION

Figure 1A:
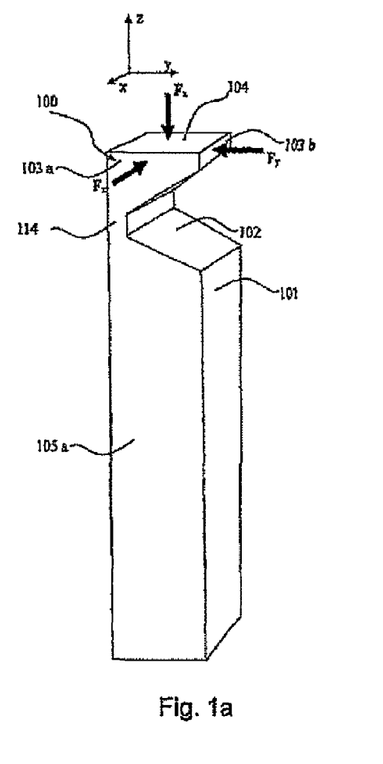
FIG. 1a shows a basic schematic view of the sensor according to the invention in a first embodiment with an incision on one side, such as can be produced for example by anisotropic wet-chemical etching in silicon.
Figure 1B:
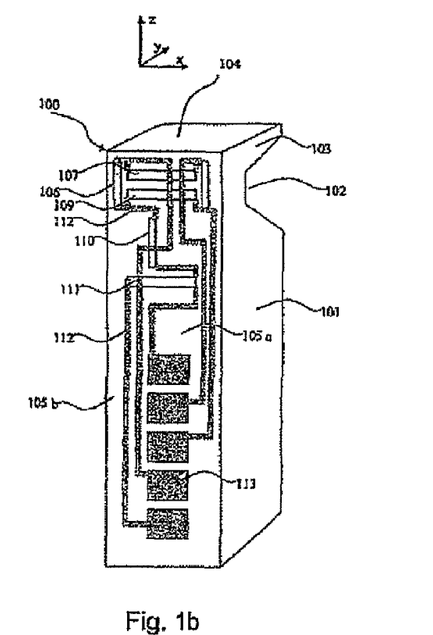
FIG. 1b shows a basic schematic view as in FIG. 1a, with illustration of the electrical functional elements such as resistors, conductor tracks and connection contacts.

The measuring element 100 according to FIGS. 1a and b comprises a silicon base body 101. A cutout 102 is introduced into the base body 101. A force $F_z$ introduced via the end face 104 brings about in the base body 101 a mechanical compressive stress as a result of compression of the base body 101. On account of the asymmetrical embodiment of the base body 101, caused by the cutout 102, a moment furthermore occurs and a flexure of the base body 101 and of the bending plate 114 thus occurs. Said moment is constant over the bending plate 114 and generates mechanical tensile stresses in the base body 101 and the bending plate 114. These tensile stresses are superposed on the compressive stress resulting from the compression and overcompensate for said compressive stress, such that a resultant tensile stress arises in the base body 101, but primarily in the bending plate 114. Therefore, mechanical tensile stresses can be measured at the top side of the base body 101 with the resistors $R_1$ to $R_6$ introduced by doping. The force component $F_z$ can be measured by means of the resistance change of the individual resistors and by means of a bridge diagonal voltage.

In the event of a lateral force action $F_x$, the resistance of the resistors $R_5$ and $R_6$ changes. On account of the lateral flexure of the measuring element 101 and of the plate 114 as a result of the force $F_x$, the resistor $R_4$ is subjected to a compressive stress and the resistor $R_2$ is subjected to a tensile stress. As a result, the resistance value of resistor $R_4$ decreases and the resistance value of resistor $R_2$ increases. Consequently, the bridge diagonal voltage also changes in the event of the loading of the measuring element 100 with a force $F_x$. With knowledge of the difference in the resistance change of the resistors $R_2$ and $R_4$, the force component $F_x$ can be determined. The resistance change of the resistors $R_3$ and $R_1$ remains small in the event of a loading of the measuring element 100 with a force $F_z$. For measuring the individual resistance change, a method is proposed such that lateral forces $F_x$ and $F_y$ can also be measured alongside the axial forces $F_z$.

If a force $F_y$ is impressed into the measuring element 100 via the radial end face 103 in FIG. 1a, a further lateral flexure of the base body 100 arises. A moment arises whose magnitude increases linearly with the distance from the force introduction location. Mechanical tensile stresses arise as a result of this, and these can be measured by means of the resistors $R_1$ to $R_6$. On account of the non-constant moment profile along the axial length of the measuring element, the resistors experience different resistance changes. By measuring the mechanical stress state at least two points distributed on the length of the base body 101, the moment profile can be determined and the force $F_y$ can thus be determined. By way of example, the difference in the resistance change of the resistors $R_1$ and $R_3$ can be used for this purpose. A higher measuring accuracy can be obtained if the measuring resistors are as far away from one another as possible in the axial direction at the distance Δx. For this purpose, in addition to the bridge resistors $R_1$ to $R_4$, the resistors $R_5$ and $R_6$ are introduced, which are connected up here to form a voltage divider, for example, and ate not necessarily located in the vicinity of the incision 102. The resistors $R_5$ and $R_6$ are optimally fitted at the location at which the tensile and compressive stresses which arise as a result of the force $F_z$ just compensate for one another. Alternative resistor arrangements are possible.

Figure 2:
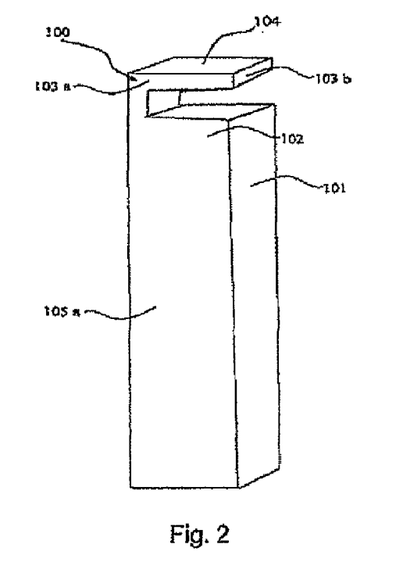
FIG. 2 shows a basic schematic view of the base body with an incision on one side such as can be produced for example by dry etching from the rear side of the wafer.

In FIG. 2, the cutout 102 in the base body 101 is produced by a method with a very high aspect ratio, for example by means of a dry etching step from the rear side of the wafer. The high aspect ratio of the steep etching edge of the cutout 102 makes it possible to position the cutout 102 very close to the top plate 104 in order thus to measure axial forces $F_z$ very sensitively with the measuring element, but to obtain a low sensitivity for lateral forces $F_x$ and $F_y$.

Figure 3:
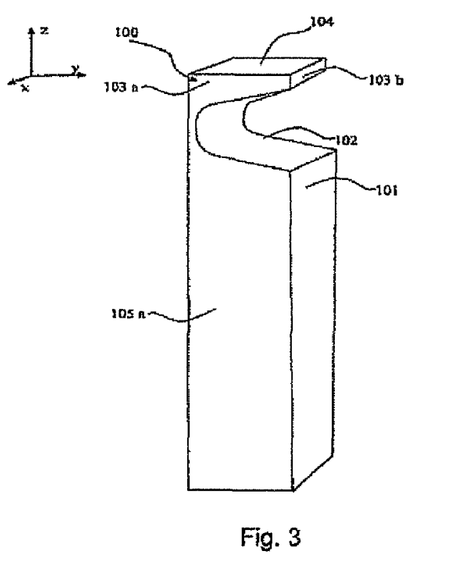
FIG. 3 shows a basic schematic view of the base body with an incision on one side such as can be produced for example by sawing.

In a further embodiment according to FIG. 3, the incision of the base body is produced by sawing from the rear side of the base body. Sawing is a very expedient method for the production of the measuring element since sawing is generally used for singulating the patterned measuring elements from the wafer. Furthermore, a virtually perpendicular edge of the cutout 102 can be produced. Therefore, the cutout 102 can be introduced closer to the top plate of the base body 101. This increases the functionality of the measuring element since lateral moments have a smaller influence on the measurement result. Furthermore, a plurality of process steps are obviated during the patterning of the incision since a patterning of an etching mask on the rear side of the wafer can be obviated. These steps are specifically a plurality of cleaning steps, the application and patterning of the etching mask, the etching, etc. The method can be carried out with known wafer saws. In order to increase the stability of the measuring element, a brief chemical etching step can subsequently be effected in order to reduce microcracks, for which purpose it is not necessary for the rear side to be masked, nor are there the stringent requirements made of the accuracy as in known structure etching steps mentioned above.

Figure 4:
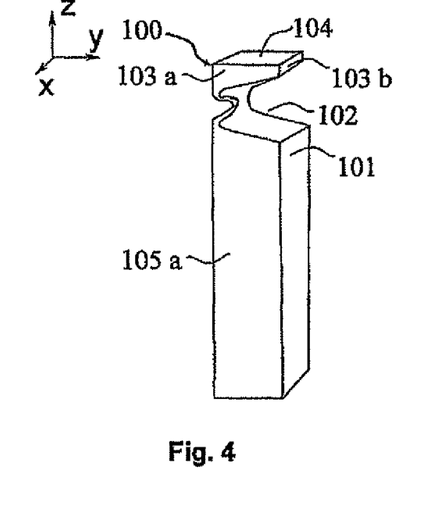
FIG. 4 shows a basic schematic view of the base body with an incision on more than one side such as can be produced for example by etching or drilling on more than one side.

In a further embodiment according to FIG. 4, the cutout 102 for producing the asymmetry of the base body is produced not only by a straight incision on the rear side of the wafer, but for example by drilling or special etching holes from the rear side of the wafer or from the front side of the wafer. A higher asymmetry of the base body 101 arises. The measuring effect is increased further as a result of this.

Figure 5:
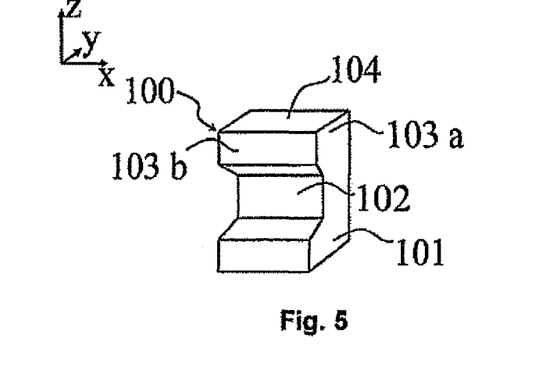
FIG. 5 shows a basic schematic view of the base body such as can be produced from a known pressure sensor by separation of the edge regions on two sides.

A possibility of producing functional prototypes arises as a result of the embodiment according to FIG. 5 as a result of the reworking of measuring elements used as standard in pressure measuring technology. A thinning of the base body below the measuring resistors is obtained here by means of an etching process. By their nature, these measuring elements always have a stable edge structure. By removing these edge regions, this structure can be converted into a structure according to the invention. It is possible to use standard pressure sensors having straight or oblique side walls. For this purpose, it is necessary to separate or interrupt the existing carrier or to directly use measuring elements without a carrier. A structure according to FIG. 5 can be produced by separating or interrupting two parallel side walls. The side faces can be separated by sawing, grinding, etching or another microtechnical processing method. This processing can be carried out on the individual element, for which purpose the latter is fixed with the bending plate on a carrier in order to protect the sensitive bending plate against damage. A cyano acrylate adhesive, for example, can be used for fixing purposes, which adhesive can be stripped away, for example by acetone, after the processing of the measuring element. The side faces as far as the bending plate can also be removed by a grinding method for example with granulations of around 1000. For series production, fabrication in the panel is possible, for which purpose standard sawing methods can be used.

Figure 6:
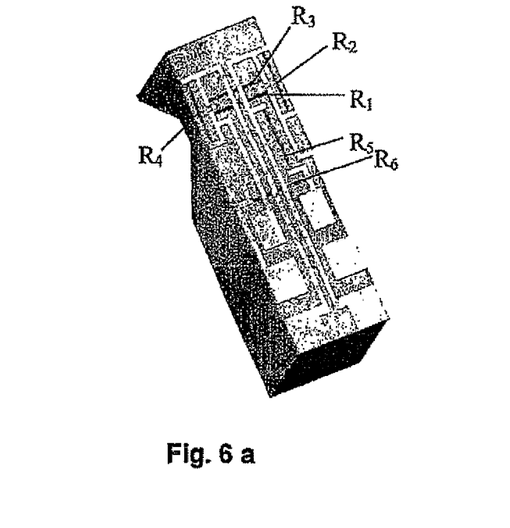
FIG. 6a shows a CAD drawing of a designed sensor element.
FIG. 6b shows a CAD drawing of a designed sensor element which has been mounted on a guide wire and housed by potting or injection-molding encapsulation with a soft, biocompatible plastic.

A CAD drawing of a sensor according to the invention which has been optimized for integration into a guide wire having a diameter of 360 μm is shown in FIG. 6a.

FIG. 6b illustrates an electrically contact-connected sensor integrated into the tip of a guide wire. Here the housing is effected by a potting with a relatively soft, biocompatible material, for example silicone or polyurethane. The high stiffness of the measuring element in comparison with the housing material ensures that the housing has a small influence on the measurement signal. This is verified by measurement results of a housed prototype according to FIG. 7.

Figure 7:
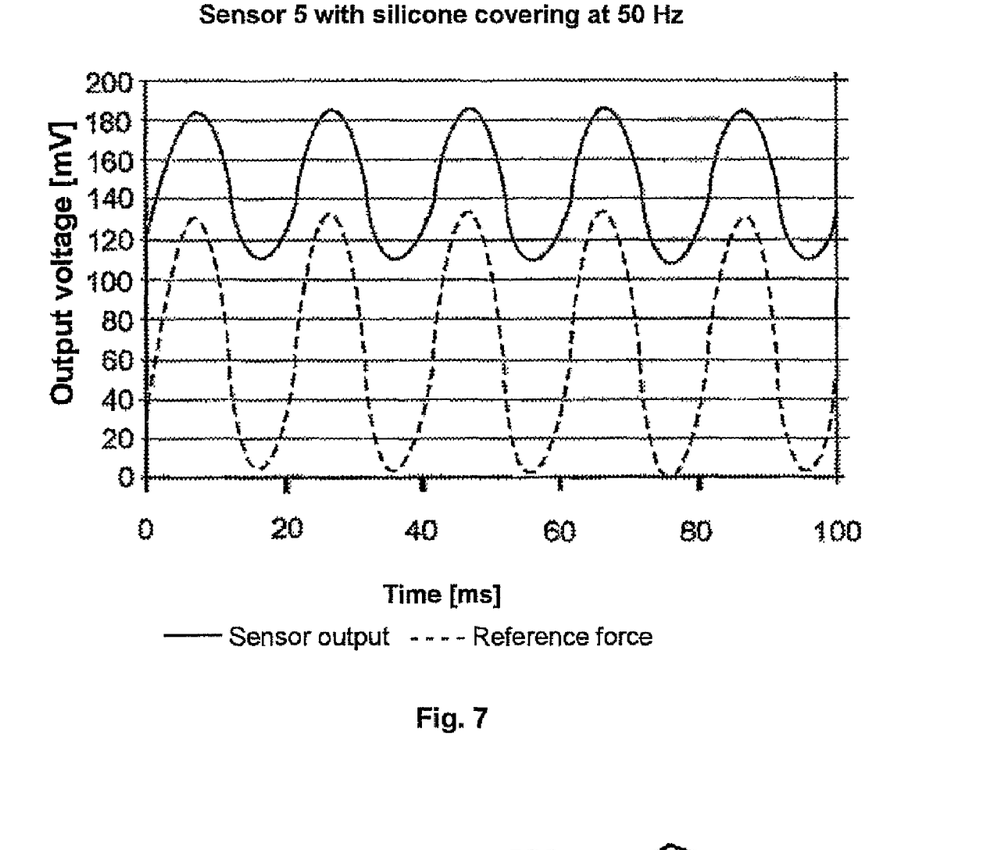
FIG. 7 shows measurement results of the signal output of a prototype for dynamic, harmonic force introduction.

FIG. 7 shows measurement results of a sensor according to the invention after housing with a silicone potting compound. The illustration shows the output signal of the sensor upon excitation with a force $F_z$ in the axial direction. The reproducible force influence can be discerned.

Figure 8:
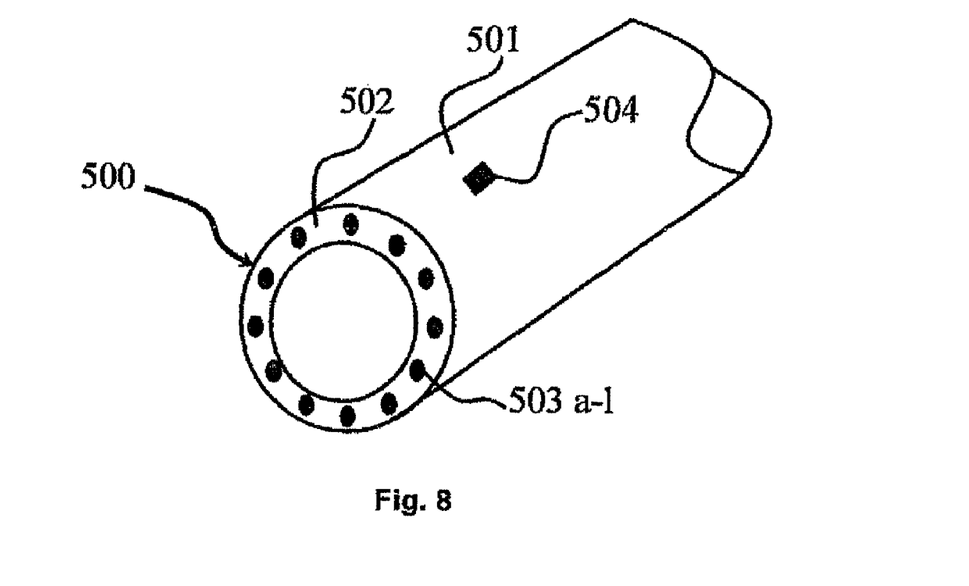
FIG. 8 shows a basic schematic diagram of a section through a catheter with integrated force sensors.

FIG. 8 illustrates a possibility for also integrating the sensors into catheter tubes. A section through the catheter tip is illustrated. The sensors are integrated into the catheter, for example by injection-molding encapsulation during the production of the catheter. The distal opening of the catheter is fully maintained by virtue of the high miniaturization of the sensors. The force sensors according to the invention are preferably introduced or fitted at the distal end of the elongated device, or else at any desired location on or in the elongated device.

On account of the simpler production, the resistors are generally introduced on the top side of the measuring element rather than in depressions in the silicon wafer, as will also be assumed below. A increase in the measuring sensitivity can be achieved in the sensor according to the invention, however, if the resistors are introduced on the rear side of the bending plate in the incision, for example by patterning with thick-film resist. As a result, a positive compressive stress is formed in the event of force loading with the force $F_z$ as a result of the bending of the base body on the rear side of the bending plate, said compressive stress being added to the positive compressive stress of the compressive effect of the force $F_z$. The two therefore support each other.

It is also possible to fit an evaluation electronic unit directly on or at the measuring element. Advantages can be obtained for example by an increased signal voltage being generated by means of a preamplification. As a result, the signal-to-noise power ratio (SNR) rises and therefore so does the resolution. By means of coded or modulated transmission of the signals or by means of voltage-proportional current conversion, in the case of integrated electronics it is possible to transmit the signals with a smaller influence of the lead. The integration of constant-voltage sources makes it possible to realize a constant-voltage feed, such that the resolution for lateral force components is increased without the line resistance having an appreciable influence on the measurement result. Furthermore, an integrated electronic unit makes it possible to directly measure electrical difference voltages at the resistors and thus to determine the direction and the magnitude of forces very accurately. An integrated electronic unit makes it possible to effect a potential matching of the signals on the chip and to refer electrical difference voltages to an individual ground line. Electrical lines can be saved as a result of this. The assembly outlay and thus the production costs of the entire device decrease as a result. The space requirement of the lines is furthermore reduced, whereby a further miniaturization of the diameter of the elongated device becomes possible. The modulation of the signals in a primary electronic unit integrated in the measuring element makes it possible to reduce the number of lines to two, and specifically to one line. A wireless transmission of power and signal is also possible by integrating a wireless transmitting unit.

Finally, the invention relates to a method for determining the magnitude of the force acting on the elongated device. Further embodiments of this method make it possible, in particular, to determine the force according to magnitude and direction.

A method will be described below which makes it possible to measure three independent force components—$F_x$, $F_y$ and $F_z$—by using a Wheatstone bridge circuit according to FIGS. 9-11 in conjunction with the sensor according to the invention. In an embodiment according to FIG. 10, an additional voltage divider is used in order to further reduce the remaining measurement uncertainty for distinguishing the forces from the x direction and z direction.

Figure 10:
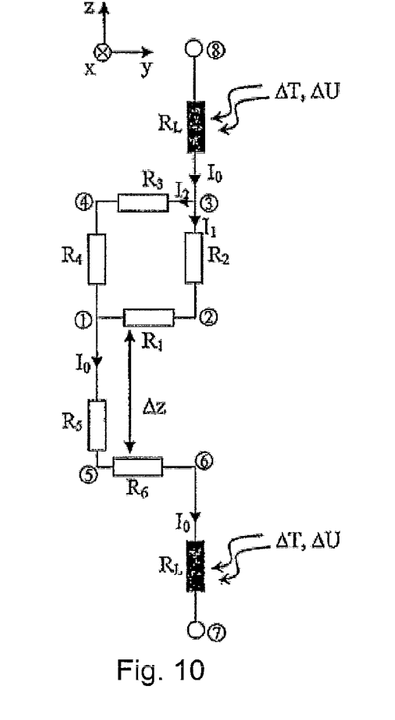
FIG. 10 shows the interconnection of the resistors as an embodiment as a full bridge with an additional voltage divider.

In a first embodiment of a method for determining the force components, the resistance values $R_1$ to $R_6$ are deduced by current and voltage measurement between the contact-connectable points 2, 4, 5, 7 and 8 in FIG. 10, the power supply being effected continuously via fixedly chosen connections. This enables the force vector present to be determined continuously.

Figure 11:
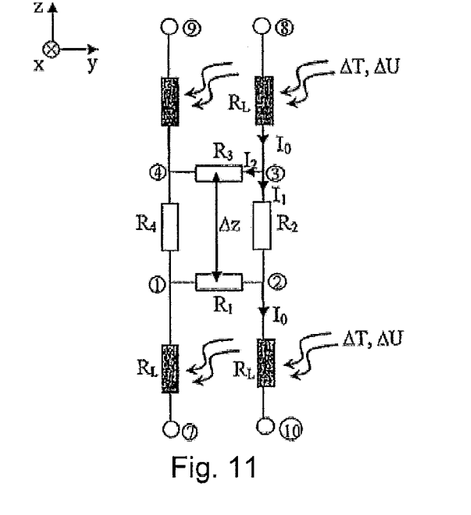
FIG. 11 shows the interconnection of the resistors with an embodiment as a full bridge, with all the line resistances for evaluation by switching.

In a second embodiment of the application of the sensor, the current and/or voltage supply and also the signal lines of the measuring element are changed by an electronic unit alternately between the points 7-10 in FIG. 11 in different combinations or the signal line is connected relative to ground at certain times. The resistance values can be determined particularly accurately by this means. The detection of the force vector thereby becomes time-discrete and an adaptation of the overall system comprising sensor, power and signal lines and electronic unit has to be adapted to the required frequency resolution of the application in order to ensure a quasi-continuous representation of the force vector.

The mathematical relationships underlying the method are dependent on the type of power feeding of the measuring bridge used. On account of the long length of the generally very thin lead wires, on account of the resultant high basic resistance of the line and the associated thermal resistance change during the application, current feeding of the resistors is preferred. Constant-current feeding is therefore assumed for the explanation of the method. Feeding with a constant voltage is likewise possible, but methods in which the measuring resistors are fed with a temporally variable power supply, for example with a sinusoidal or rectangular signal and power flow, can also be employed. The relationships can then be adapted by an expert by simple calculations.

Figure 9:
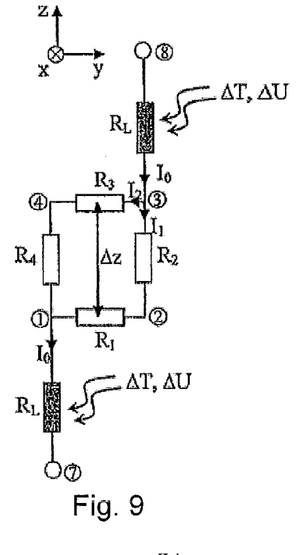
FIG. 9 shows the interconnection of the resistors, specifically the embodiment as a full bridge.

For the description of the first embodiment of the application of the force sensor according to the invention, FIG. 9 schematically presents the electrical construction when the measuring resistors are interconnected to form a Wheatstone full bridge. The resistance of the lead is additionally included, this resistance being varied by external temperature influences $\Delta T$. Furthermore, electromagnetic interference is coupled in via the lines. Said interference is designated by $\Delta U$. The output voltage is normally measured at high impedance, for which reason line resistances can be disregarded in the first case for the output voltage and are not illustrated.

The way in which different force components can be measured with the aid of the electrical voltages at the resistor arrangements illustrated in FIG. 9 is demonstrated below. Given a predetermined current intensity $I_0$ and identical basic resistances $R_0$, the currents in the bridge branches result as $$I_1 = \frac{R_1 + \Delta R_1 + R_2 + \Delta R_2}{R_1 + \Delta R_1 + R_2 + \Delta R_2 + R_3 + \Delta R_3 + R_4 + \Delta R_4} \cdot I_0 \quad \text{(Equation 1)}$$

$$= \frac{1}{2} \cdot \frac{\left(1 + \frac{\Delta R_1 + \Delta R_2}{2 \cdot R_0}\right)}{\left(1 + \frac{\Delta R_1 + \Delta R_2 + \Delta R_3 + \Delta R_4}{4 \cdot R_0}\right)} \cdot I_0$$

In this case, the resistance change is linked to the mechanical stresses by way of the piezoresistive effect. The following holds true in a simplified fashion for the measuring elements shown $$\frac{\Delta R_i}{R_0} = \pi_{longitudinal} \cdot T_{longitudinal} + \pi_{transverse} \cdot T_{transverse} \quad \text{(Equation 2)}$$

where $T_{longitudinal}$ and $T_{transverse}$ designate the mechanical stresses longitudinally and transversely with respect to the resistor orientation. $\pi_{longitudinal}$ and $\pi_{transverse}$ are the assigned piezoresistive coefficients.

$I_2$ can be calculated analogously to $I_1$, or the following holds true also in a simple fashion $$I_2 = I_0 - I_1 \quad \text{(Equation 3)}$$

In a measuring bridge according to FIG. 10 the voltages between all four external connections of the bridge resistance can be determined with these currents. For the bridge diagonal voltage at the points 2 and 4, disregarding the quadratic components of the small resistance changes relative to the basic resistance, the following relationship results $$U_{2,4} = U_2 - U_4 \quad \text{(Equation 4)}$$

$$= R_0\left(1 + \frac{\Delta R_2}{R_0}\right) \cdot I_1 - R_0\left(1 + \frac{\Delta R_4}{R_0}\right) \cdot I_2$$

$$\approx \frac{\frac{1}{4}\left(\frac{-\Delta R_1 + \Delta R_2 - \Delta R_3 + \Delta R_4}{R_0}\right)}{\left(1 + \frac{\Delta R_1 + \Delta R_2 + \Delta R_3 + \Delta R_4}{4 \cdot R_0}\right)} \cdot R_0 \cdot I_0$$

The electrical voltage $U_{2,4}$ between the points 2 and 4 is a measure of the mechanical stress in the axial measuring element direction, which is primarily established as a result of the forces $F_z$ and $F_y$. If the portion of the mechanical stress is known from the portion from $F_y$, then the portion in $F_z$ and thus $F_z$ itself can also be determined.

Furthermore, the voltages between the points 4 and 8 and also between the points 2 and 7 are accessible. They result in the following manner:

$$U_{4,8} = R_3 \cdot I_2 + R_L \cdot I_0 \quad \text{(Equation 5)}$$

$$\approx \left(\frac{\frac{1}{2} \cdot R_0 \cdot \left(1 + \frac{2 \cdot \Delta R_3 + \Delta R_1 + \Delta R_2}{2 \cdot R_0}\right)}{\left(1 + \frac{\Delta R_1 + \Delta R_2 + \Delta R_3 + \Delta R_4}{4 \cdot R_0}\right)} + R_L\right) \cdot I_0$$

and $$U_{2,7} = R_1 \cdot I_1 + R_L \cdot I_0 \quad \text{(Equation 6)}$$

$$\approx \left(\frac{\frac{1}{2} \cdot R_0 \cdot \left(1 + \frac{2 \cdot \Delta R_1 + \Delta R_3 + \Delta R_4}{2 \cdot R_0}\right)}{\left(1 + \frac{\Delta R_1 + \Delta R_2 + \Delta R_3 + \Delta R_4}{4 \cdot R_0}\right)} + R_L\right) \cdot I_0$$

By forming the difference between the two voltages $U_{4,8}$ and $U_{2,7}$ in an electronic unit, it is possible to eliminate the offset portion of the two voltages, which arises as a result of the basic resistance $R_0$ and the symmetrical line resistance $R_L$, and also coupling in an electromagnetic interference. This results predominantly in a difference between the resistance changes of $R_1$ and $R_3$. This difference voltage is a measure of the moment present about the y axis and hence a measure of the force $F_y$, which can be determined therefrom.

Thus, the force $F_y$ is known and the signal obtained from the bridge diagonal voltage can be reduced by the portion of the effect of $F_y$, such that the effect of $F_z$ predominantly results and $F_z$ is therefore also known.

Similar equations can be formulated for the transversely arranged resistors:

$$U_{4,7} = R_4 \cdot I_2 + R_L \cdot I_0 \quad \text{(Equation 7)}$$

$$\approx \left(\frac{\frac{1}{2} \cdot R_0 \cdot \left(1 + \frac{2 \cdot \Delta R_4 + \Delta R_1 + \Delta R_2}{2 \cdot R_0}\right)}{\left(1 + \frac{\Delta R_1 + \Delta R_2 + \Delta R_3 + \Delta R_4}{4 \cdot R_0}\right)} + R_L\right) \cdot I_0$$

and $$U_{2,8} = R_2 \cdot I_1 + R_L \cdot I_0 \quad \text{(Equation 8)}$$

$$\approx \left(\frac{\frac{1}{2} \cdot R_0 \cdot \left(1 + \frac{2 \cdot \Delta R_2 + \Delta R_3 + \Delta R_4}{2 \cdot R_0}\right)}{\left(1 + \frac{\Delta R_1 + \Delta R_2 + \Delta R_3 + \Delta R_4}{4 \cdot R_0}\right)} + R_L\right) \cdot I_0$$

By forming the difference between the two voltages $U_{4,7}$ and $U_{2,8}$ in an electronic unit, it is once again possible to eliminate the offset portion of the two voltages, which arises as a result of the basic resistance $R_0$ and the symmetrical line resistance $R_L$. It can readily be discerned that in the event of an opposite change in the resistances $R_2$ and $R_4$, as arises in the event of loading of the measuring element with a force $F_x$, the difference between the voltages $U_{4,7}$ and $U_{2,8}$ increases, whereby the force $F_x$ can be determined.

As a result of using the piezoresistive coupling equation, the three voltages $U_{4,6}$, $U_{4,2}$ and $U_{2,7}$ form three independent equations influenced by the three forces $F_x$, $F_y$ and $F_z$ by way of the sensor geometry. These equations can be determined not only by analytical calculations but also by FEM simulations taking account of the piezoresistive effect and the electrical coupling, or can be determined on the real sensor by measurement. Since three independent electrical voltages are measured, the linear equation system can be solved by addition and multiplication of the voltages in such a way that $F_x$, $F_y$ and $F_z$ can be determined individually. Consequently, the three force components are measurable in terms of direction and amplitude. In a practical implementation, therefore, the individual force components $F_x$, $F_y$ and $F_z$ can be extracted for example by means of analogue adders and amplifiers or alternatively digitally.

The described measuring method for measuring a plurality of force components is possible with a Wheatstone bridge without changes and without the use of additional lines. The resolution for the main component $F_z$, which is given by the bridge diagonal voltage $U_{2,4}$, is not reduced. Care should be taken to ensure that the resistors $R_1$ and $R_3$ in the specific case present here are arranged at a corresponding distance $\Delta z$ in order to detect a sufficiently large difference between the mechanical normal stresses caused by the force component $F_x$.

The resolution for forces from the y direction can be increased by fitting an additional resistor arrangement at the distance $\Delta z$ according to FIG. 11 on the measuring element. In FIG. 11 this is for example an additional voltage divider comprising piezoresistive resistors such as is represented on the real measuring element by the resistors $R_5$ and $R_6$ in FIG. 1b. The force component $F_y$ can then be resolved more accurately on account of the larger distance $\Delta z$ and the higher sensitivity of the voltage divider. By way of example, the difference in the electrical voltage at the points 4 and 5 in FIG.

11 can be used for this purpose, but other combinations of the electrical voltages are also possible.

Similar relationships can be found for voltage feeding of the bridge, the voltage divider rule simply being employed in order to determine the relevant equations. Higher transfer factors should then be expected for the lateral force components $F_y$ and $F_x$, but also a dependence of the bridge diagonal voltage on the line resistance.

Additional information about the resistance change of the individual resistors can be derived by measuring the internal resistance of the bridge circuit. For this purpose, known resistors can be fitted at the external connections of the signal lines and a current flow can thus be deliberately permitted via the signal lines. This current is dependent on all four resistors and the external resistors in parallel with the bridge. It is possible to realize an evaluation circuit with constant or temporally variable external resistance values. Instead of external resistors, it is also possible to use current sources in the signal lines for loading the bridge in order to determine the internal resistances by means of the potential of the bridge diagonal voltage.

Further information about the resistance change can be derived with the aid of further boundary conditions, for example the assumption of a constant total bridge resistance with mechanical loading.

In a further embodiment of the application of the force sensor it is also possible for the lines of the bridge circuit according to FIG. 9 to be connected only individually in a temporal sequence by means of an external electronic unit, or for the power lines and signal lines to be interchanged periodically or stochastically during operation. Different sensitivities for different force directions can thereby be obtained. The line resistances of the signal lines then also have to be taken into account since at certain times they represent power lines and carry current. The complete equivalent circuit diagram is illustrated in FIG. 11. The functioning is simple. By way of example, a total bridge resistance added to the line resistance can be determined via the connections at the points 7 and 8 in FIG. 12. By means of a temporally offset resistance measurement between the points 10 and 9, it is possible to determine a further total resistance, which generally does not correspond to the previously measured resistance between the points 7 and 8. The two total resistances can be described by mathematical functions of the bridge resistances. These equations represent independent linear combinations of the resistance changes and the force components. The change in the individual resistances can be calculated with the aid of further measurements in the same way between the points 7 to 10.

Furthermore, it is also possible to determine the resistance between adjacent connections in FIG. 12, such that the measured resistance corresponds to the parallel interconnection of the resistance directly present with the remaining resistances, added to the line resistances.

It is also possible, by means of an evaluation circuit, by switching the signal line with respect to ground, to bring about a short circuit of the resistors then connected to ground on one side. This can be done for example in a manner such that the supply voltage is permanently present at point 8 according to FIG. 11; ground potential is permanently present at point 7. By temporarily connecting the points 9 and 10 to ground potential and simultaneously measuring the current flow through the points 9 and 10, it is possible to determine the resistance values $R_2$ and $R_3$. The normal function of the bridge can be reestablished by opening the switches. By measuring the electrical voltage for example between the points 7 and 10 and also the points 7 and 4, it is then possible to determine the remaining resistance values $R_1$ and $R_4$. The values of all four resistances are thus known. In order to increase the measuring accuracy, it is possible to perform further measurements, for example between the points 10 and 8 and also between the points 9 and 8, and thus to reduce the influence of the line resistance, particularly when the line resistance $R_L$ has the same value in all of the lines.

The resistance change of individual resistors can be determined particularly simply and accurately if an open bridge is used. This can be employed particularly advantageously when the line resistances $R_L$ are low, since an asymmetry of the bridge interconnection otherwise arises on account of the line resistances. Furthermore, at least one further lead should be integrated in the embodiment as an open bridge.

It is readily possible for an expert to specify the relationships between electrical voltages and currents and to design one of diverse options for the circuit structure which can be used to deduce the resistance change of individual resistors. In this way, in combination with the force sensor according to the invention, independent force components can be measured and the force vector can thus be determined.

The invention claimed is:

1. A force sensor for detecting at least a force acting in a longitudinal direction of a catheter or guide wire, the force sensor comprising a force pick-up for detecting the force, wherein the force pick-up comprises:
   a base body with an end face, wherein the base body includes at least one cutout, wherein the cutout causes an asymmetry of the base body relative to the longitudinal direction of the catheter or guide wire upon flexing of the base body upon force $F_z$ loading thereon from an axial direction, wherein the end face includes a surface area that is substantially greater than the cross-sectional area of the base body in the region of the cutout, but not substantially smaller than the cross-section of the rest of the base body;
   one or more stress/strain-sensitive resistors; and
   an electrical connection area disposed in a non-perpendicular configuration with respect to the axial direction of the catheter or guide wire for fitting the sensor to the catheter or guide wire.

2. The force sensor as claimed in claim 1, wherein the force sensor is further configured to measure a lateral acting force $F_x$.

3. The force sensor as claimed in claim 2, wherein the base body is comprised of silicon and the one or more resistors are integrated monolithically.

4. The force sensor as claimed in claim 3, wherein the one or more resistors are disposed on a top side or an underside of a bending plate of the base body.

5. The force sensor as claimed in claim 4, further comprising at least one resistor for each force component to be measured.

6. The force sensor as claimed in claim 5, comprising a further resistor or resistor arrangement for determining force components $F_z$ and $F_x$ from a difference between the resistance changes.

7. The force sensor as claimed in claim 6, wherein the further resistor or resistor arrangement are bridge resistors disposed at an increased distance such that the effects of the lateral force components $F_z$ and $F_x$ are distinguished with greater accuracy from the difference between the resistance changes.

8. The force sensor as claimed in claim 7, wherein the further resistor or resistor arrangement is disposed at the location at which at least one resistor or a resistor arrangement results in a minimum measurement signal for the force component $F_z$.

9. The force sensor as claimed in claim 4, wherein the one or more resistors are connected at least in part to form Wheatstone bridge circuits in an open or closed configuration.

10. The force sensor as claimed in claim 1, wherein the angle of the cutout is between 30° and 150°.

11. The force sensor as claimed in claim 1, wherein the cutout extends through more than one side of the base body.

12. The force sensor as claimed in claim 1, wherein the end face is of a rectilinear or round cross-section.

13. The force sensor as claimed in claim 1, further having integrated therein an electronic unit for signal processing, power feeding, or data transmission.

14. The force sensor as claimed in claim 1, wherein the base body is comprised of a material other than silicon and includes strain gauges for measuring strain or stress.

15. A method for using a force sensor for determining a force vector with magnitude and direction using a Wheatstone bridge arrangement comprising the steps of
   providing a force pick-up for detecting the force, wherein the force pick-up comprises:
      a base body with an end face, wherein the base body includes at least one cutout, wherein the cutout causes an asymmetry of the base body relative to the longitudinal direction of a catheter or guide wire upon flexing of the base body upon force $F_z$ loading thereon from an axial direction, wherein the end face includes a surface area that is substantially greater than the cross-sectional area of the base body in the region of the cutout, but not substantially smaller than the cross-section of the rest of the base body;
      one or more stress/strain-sensitive resistors disposed on a top side or an underside of the end face, wherein the one or more resistors are connected at least in part to form Wheatstone bridge circuits in an open or closed configuration;
      an electrical connection area disposed in a non-perpendicular configuration with respect to the axial direction of the catheter or guide wire for fitting the sensor to the catheter or guide wire; and
      means for measure a lateral acting force $F_x$; and
   detecting a change in individual resistances also alongside a bridge diagonal voltage.

16. The method as claimed in claim 15, wherein the total bridge resistance is measured to affect an evaluation of the mechanical stresses against the force sensor.

17. The method as claimed in claim 15, further comprising the step of using electrical difference voltages between accessible contact points of the bridge circuits and line currents for continuously determining the force vector.

18. The method as claimed in claim 15, wherein the resistance of the one or more resistors is effected by temporally variable interconnection/contact-connection thereof, wherein the temporally variable interconnection/contact-connection is effected periodically or randomly and automatically, and wherein the temporally variable interconnection of the resistors is effected by switching in an external electronic unit or by switches or modulators integrated on the force sensor, wherein power supply lines and signal lines are exchanged in a time-dependent manner or are configured independently.

19. The method as claimed in claim 15, wherein data corresponding to the force vector is transmitted in a modulated, multiplexed, or other coded fashion, wherein the one or more resistors are fed with a current or a voltage of constant amplitude or specific frequency, and wherein the signal processing is effected by analog or digital means.

* * * * *